(12) United States Patent
Muller et al.

(10) Patent No.: US 9,797,834 B2
(45) Date of Patent: Oct. 24, 2017

(54) ARRANGEMENT FOR OPTICALLY MEASURING ONE OR MORE PHYSICAL, CHEMICAL AND/OR BIOLOGICAL, PROCESS VARIABLES OF A MEDIUM

(71) Applicant: Endress + Hauser Conducta Gesellschaft für Mess- und Regeltechnik mbH + Co. KG, Gerlingen (DE)

(72) Inventors: Andreas Muller, Ostfildern (DE); Thilo Kratschmer, Gerlingen (DE); Matthias Grossmann, Vaihingen-Enz (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 0 days.

(21) Appl. No.: 14/252,091

(22) Filed: Apr. 14, 2014

(65) Prior Publication Data

US 2015/0293019 A1   Oct. 15, 2015

(30) Foreign Application Priority Data

Apr. 15, 2013   (DE) .................. 10 2013 103 735

(51) Int. Cl.
*G01N 21/53*   (2006.01)
*G01N 15/06*   (2006.01)
(Continued)

(52) U.S. Cl.
CPC .............. *G01N 21/53* (2013.01); *G01N 15/06* (2013.01); *G01N 21/8507* (2013.01);
(Continued)

(58) Field of Classification Search
CPC ...................................................... G01N 21/53
(Continued)

(56) References Cited

U.S. PATENT DOCUMENTS 3,665,201 A    5/1972   Shea et al.
3,680,962 A *  8/1972   Hayakawa ........... G01N 21/532
                                                250/574
(Continued)

FOREIGN PATENT DOCUMENTS

AT     264872 B    9/1968
CH     670513 A5   6/1989
(Continued)

OTHER PUBLICATIONS

Nov. 5, 2013 German Search Report, German Patent Office, Munich, Germany.

*Primary Examiner* — Tarifur Chowdhury
*Assistant Examiner* — Omar Nixon
(74) *Attorney, Agent, or Firm* — Christopher R. Powers; PatServe

(57) ABSTRACT

A turbidity sensor or an arrangement for optically measuring one or more physical, chemical and/or biological, process variables of a medium. The medium is located in a pipe. The arrangement includes a housing and the housing is embodied for securement in the pipe. The housing is embodied for accommodating at least one light source for sending light through a window region into the medium and at least one light receiver for receiving light through the window region from the medium. The light is scattered by the medium and the light intensity received by the light receiver is a measure for the physical, chemical and/or biological, process variable, characterized in that the light source is so arranged that the light propagates in the medium in the longitudinal direction of the pipe.

18 Claims, 3 Drawing Sheets

(51) Int. Cl.
   *G01N 33/18* (2006.01)
   *G01N 21/85* (2006.01)
   *G01N 15/00* (2006.01)
   *G01N 21/15* (2006.01)

(52) U.S. Cl.
   CPC ............ *G01N 33/18* (2013.01); *G01N 21/15* (2013.01); *G01N 2015/0053* (2013.01); *G01N 2015/0065* (2013.01); *G01N 2015/0693* (2013.01); *G01N 2201/062* (2013.01)

(58) Field of Classification Search
   USPC ........................................................ 356/339
   See application file for complete search history.

(56) References Cited

U.S. PATENT DOCUMENTS

| | | | |
|---|---|---|---|
| 4,874,243 A | | 10/1989 | Perren |
| 5,453,832 A | | 9/1995 | Joyce |
| 5,489,977 A | * | 2/1996 | Winslow et al. ............... 356/73 |
| 7,411,668 B2 | * | 8/2008 | Klinkhammer ........ G01N 21/05 356/213 |
| 7,663,751 B1 | * | 2/2010 | Mitchell ....................... 356/339 |
| 2006/0103842 A1 | * | 5/2006 | Tokhtuev et al. ............. 356/338 |
| 2012/0242993 A1 | * | 9/2012 | Schick ................ G01N 21/532 356/442 |

FOREIGN PATENT DOCUMENTS

| | | |
|---|---|---|
| DE | 4233218 A1 | 4/1994 |
| DE | 69129937 T2 | 12/1998 |

* cited by examiner

ARRANGEMENT FOR OPTICALLY MEASURING ONE OR MORE PHYSICAL, CHEMICAL AND/OR BIOLOGICAL, PROCESS VARIABLES OF A MEDIUM

TECHNICAL FIELD

The invention relates to an arrangement for optically measuring one or more physical, chemical and/or biological, process variables of a medium. The invention relates further to a turbidity sensor.

BACKGROUND DISCUSSION

Turbidity is the lessening of the transparency of a medium, for example, a liquid, caused by the presence of undissolved substances, since light radiated into the medium is scattered on these undissolved substances. In the case of optical turbidity sensors, the turbidity value of a liquid is determined by measuring this scattered light.

Turbidity measurements in the sense of this invention are performed by means of a turbidity sensor, especially in fresh and industrial water as well as in gases. Furthermore, the invention is concerned with measurements of similar process variables such as solids content or sludge level. Measuring devices suitable for determining the corresponding process variables are manufactured and sold by the group of firms, Endress+Hauser, in a large number of variants, for example, under the designation "Turbimax CUS51D".

Usually, the sensors are arranged in housings, and the determining of the process variable occurs, such as already mentioned, optically. In such case, electromagnetic waves of a certain wavelength are sent from at least one light source, scattered by the medium being measured and the scattered waves received by a light receiver. In such case, "light" in the sense of this invention is not limited to the visible region of the electromagnetic spectrum, but, instead, can be electromagnetic radiation of any wavelength, especially also radiation in the far ultraviolet (UV) and in the infrared (IR) wavelength ranges. For example, the wavelengths of the electromagnetic waves of the optical components lie typically in the near infrared, for example, at 860 nm.

Applied as light sources are, most often, narrow band radiators, e.g. a light emitting diode (LED). In such case, the LED is used for producing light lying in a suitable wavelength range. Correspondingly applied as light receiver can be a photodiode, which produces from the received light a receiver signal, for example, a photocurrent or a photovoltage.

The sensors are installed in containments. Light scatterings or reflections on the walls of the containments corrupt the measurement signal, when such are detected by the sensor. Since the influence of these wall effects increases with declining turbidity of the medium (smaller extinction by the medium and smaller measurement signal), in the case of small clouding of the measured medium (e.g. in the clear water or drinking water domains), wall effects make turbidity measurement almost impossible.

Therefore, in practice, an effort is made to position optical sensors with as large separation as possible from walls, for example, using large volume containers.

From the point of view of the user, it is, however, often advantageous to position the sensors directly in a pipeline, respectively process line. The optical elements are, as a rule, positioned externally on the straight, right angled end face of the sensor and the transmitted light is radiated inclined into the medium. Since the sensor in the case of this tube installation is surrounded peripherally by surfaces, different disturbances result from wall effects as a function of the pipe diameter.

As a rule, it is indicated in operating instructions that the sensors should be positioned as far as possible from walls or from the floor or so to orient them that the transmitted light is not directed at wall areas or floors. It is, thus, frequently recommended that the sensor be installed inclined, i.e. at an angle relative to the pipe or containment. This positioning, for instance, at an angle of 45°, is, however, undesirable in practice, since pipe fittings, flanges etc., are, as a rule, embodied at an angle of 90° to the pipe axis.

Therefore, sensors frequently have to be readjusted in the installed state, in order to match them to the particular situation. This can occur, for instance, by the adjusting of one or more measurement points. The measurement signal corrupted by wall effects is, in such case, associated with a reference value. Another approach is to adjust the measured value as a function of the installed situation via experimentally ascertained correction factors. In other cases, sensors are coordinated with a pipe piece or a flow through cell in the plant and these delivered as matched "pairs". In all described examples, there results for the user a significant effort, which does not solve the actual problem, but, instead, at most, ameliorates it.

SUMMARY OF THE INVENTION

An object of the invention, therefore, is to achieve a minimizing of disturbing wall effects coupled with as simple as possible installation.

The object is achieved by an arrangement, wherein the arrangement includes a housing and the housing is embodied for securement in a pipe, wherein the housing is embodied for accommodating at least one light source for sending light through a window region into the medium and at least one light receiver for receiving the light through the window region from the medium, and wherein the light is scattered by the medium and the light intensity received by the light receiver is a measure for the physical, chemical and/or biological, process variable. The light source is so arranged that the light propagates in the medium in the longitudinal direction of the pipe.

The disturbing influences, which occur from reflection and scattering on the walls of containments, especially on a pipe wall, are, thus, minimized, and, in given cases, completely eliminated. Readjustments after installation of the arrangement are no longer necessary, nor are corrections by means of experimental correction factors required.

Preferably, the housing is arranged to be essentially perpendicular to the longitudinal axis of the pipe. An installation of the arrangement is, thus, simple and possible with established methods, thus, for instance, using flanges.

In an advantageous embodiment, a first interface with a medium-contacting outer surface is provided at the window region, wherein the light source is so arranged that the light propagates in the longitudinal direction of the pipe after refraction at the first interface. The light source itself, thus, does not need to be arranged in the longitudinal direction of the pipe.

In an additional advantageous embodiment, a second interface with a medium-contacting outer surface is provided at the window region, wherein the light receiver is so arranged that light scattered in the medium preferably at 90° propagates after refraction on the second interface in the direction of the light receiver. Depending on the type of application, different standards such as ISO 7027 or EPA (Environmental Protection Agency) require the measuring of the scattered light at a certain angle. Common, in such case, are 90° and/or 135° to the direction of incidence. The proposed embodiment provides that the light receiver receives 90° scattered light, even when, for instance because of refraction, the light receiver is not positioned at 90° to the direction of incidence.

In a preferred form of embodiment, the first interface and the second interface are arranged at an angle, especially at 45', to the longitudinal axis of the housing. Thus, the window region is directly flowed on by the medium and this favors a self-cleaning effect (thus, the medium cleans the window region). Also, air bubbles can automatically slide off. Furthermore, there is in the case of such an arrangement no optical crosstalk, since light from the light source cannot reach the light receiver on a direct path.

In an advantageous embodiment, all surfaces and edges of the housing in contact with the medium are smooth and rounded, in order further to facilitate self-cleaning. Also, then mechanical cleaning can be performed more easily.

In a preferred variant, the window region is step shaped and the first interface and the second interface are arranged at an angle of 90° to one another. Also, in this embodiment, disturbing wall effects are minimized and self-cleaning favored.

In order that no direct optical crosstalk from light source to light receiver can take place, the housing includes a protrusion, which is so embodied that light sent from the light source does not reach the light receiver on a direct path.

In an embodiment, the light source is arranged perpendicularly to the longitudinal axis of the housing.

In a preferred form of embodiment, the window region includes a protective shell, which is so embodied that it is transparent for the light. Especially, the window region is formed by the protective shell. The protective shell is, for instance, formed of quartz glass. By using a protective shell, the window region no longer needs to be connected with the housing by adhesive, soldering, etc.

The invention relates further to a turbidity sensor including an arrangement according to one of the above described embodiments. Preferably, the turbidity sensor is used for a low turbidity domain, e.g. for drinking water measurement.

BRIEF DESCRIPTION OF THE DRAWINGS

The invention will now be explained in greater detail based on the appended drawing, the figures of which show as follows.

DETAILED DISCUSSION IN CONJUNCTION WITH THE DRAWINGS

Figure 1A:
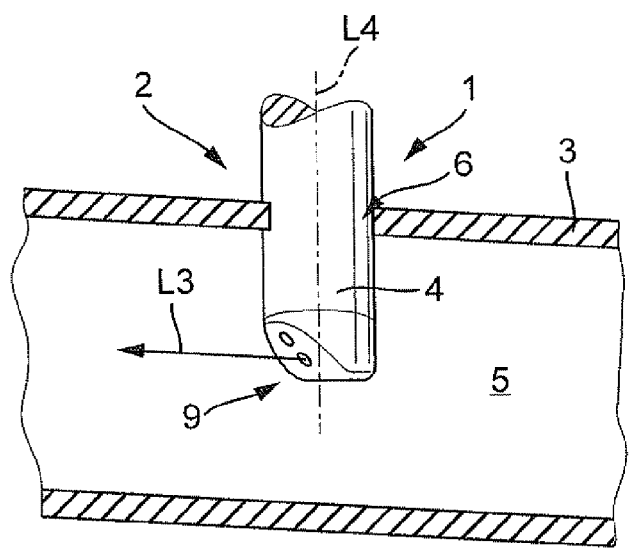
FIG. 1a the arrangement of the invention on a pipe.

In the figures, equal features are provided with equal reference characters.

The arrangement of the invention in its totality bears the reference character 1 and is presented in FIG. 1a. Without limitation, FIG. 1a shows a turbidity sensor 2, which includes an arrangement 1. Turbidity sensor 2 is arranged on a containment, especially on a pipe 3. This is accomplished via securement means 6, such as, for instance, a flange. Also, the turbidity sensor 2 can be arranged on an immersion, or retractable, assembly or the like. Located in the pipe 3 is medium 5. Especially, the medium 5 flows through the pipe 3. The medium 5 to be measured is, most often, a liquid, often water for industrial use, or waste water. The arrangement may be applied, however, also, for example, for analyzing fresh water, especially drinking water. The turbidity sensor 2 includes a housing 4 having a longitudinal axis L4. The turbidity sensor 2 is arranged essentially perpendicularly to the longitudinal axis L3 of the pipe 3.

Figure 1B:
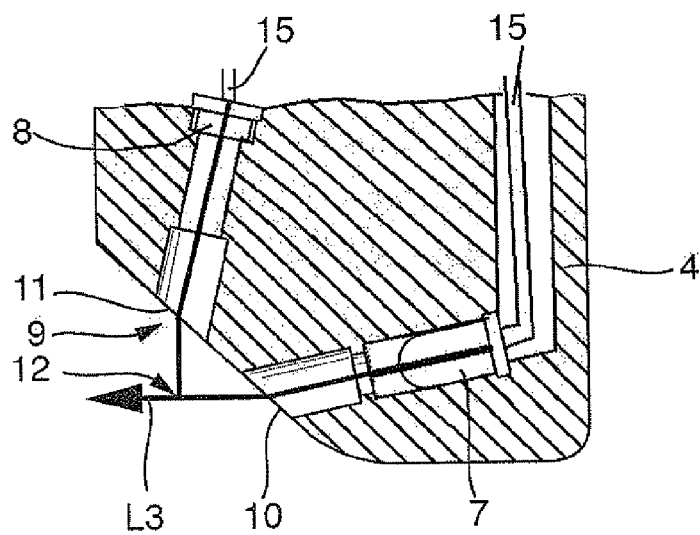
FIG. 1b the arrangement of FIG. 1a in cross section.

FIG. 1b shows a cross section through the turbidity sensor 2. For measuring at least one physical, chemical and/or biological, process variable, the arrangement 1 includes a measuring apparatus having at least one light source 7 and a light receiver 8. Via the connections 15, the light source 7 and the light receiver are connected with a control unit (not shown). The control unit can be, for instance, a measurement transmitter, a control station, etc.

The light receiver 8 is embodied, for instance, as a photodiode, which produces from the received light a receiver signal, for example, a photocurrent or a photovoltage.

The light source 7, frequently an LED, sends light in the direction of the medium 5. In such case, "light" in the sense of this invention is not limited to the visible region of the electromagnetic spectrum, but, instead, can be electromagnetic radiation of any wavelength, especially also radiation in the far ultraviolet (UV) and in the infrared (IR) wavelength ranges. Especially, a wavelength of 860 nm can be used.

The light passes from the housing 4 through an optical window region 9 transparent for the radiated light. The window region 9 is composed, for instance, of sapphire glass, quartz glass or the like. The window region 9 can be embodied as a single large window or as a plurality of small windows (one each for light source/light receiver). Window region 9 and housing 4 are rigidly connected with one another. Especially, window region 9 and housing 4 are connected with one another sealed against the medium. Window region 9 and housing 4 are connected with one another, for instance, by adhesive, solder, braze, etc.

Light source 7 is so arranged in the housing 4 that the radiated light propagates in the direction of the longitudinal axis L3 of the pipe 3. In this way, it can be prevented that light is sent in the direction of the pipe wall, such that disturbances occur.

FIG. 1a shows a first embodiment. Provided at the window region 9 is a first interface 10; see, in this connection, also FIG. 1b. The light source 7 is so arranged that the light, after refraction at the first interface 10, propagates in the longitudinal direction L3 of the pipe 3. In other words, the light source 7 is not positioned in FIG. 1b in the longitudinal direction L3 of the pipe 3 and the refraction at the interface 10 achieves that the light propagates in the longitudinal direction L3.

The light is then scattered by the medium, i.e. the medium 5 brings about a scattering 12. There are different methods for how the scattered light should then be registered. Examples include registering at 90° or 135° to the direction of incidence. FIG. 1b shows registering at an angle of 90°.

FIG. 1b shows that a second interface 11 is provided in the window region 9. The light receiver 8 is, in such case, so arranged that the scattered light propagates in the direction of the light receiver 8 after refraction at the second interface 11. In other words, the light receiver 8 is not positioned in FIG. 1b in the longitudinal direction L4 of the housing 4 and the refraction of the light scattered at 90° on the interface 11 achieves that this light propagates in the direction of the light receiver 8. There arises, thus, no optical crosstalk, since light from the light source 7 does not reach the light receiver on a direct path.

Used as materials for the arrangement 1, especially for the housing 3, can be stainless steel, synthetic material such as plastic, or a ceramic. As already mentioned, the turbidity sensor is applied frequently for drinking water and waste water analysis. The materials are so selected that they are suitable for the application, for instance, for waste water analysis. Synthetic materials must thus be correspondingly resistant synthetic materials, such as PTFE or the like.

Figure 2:
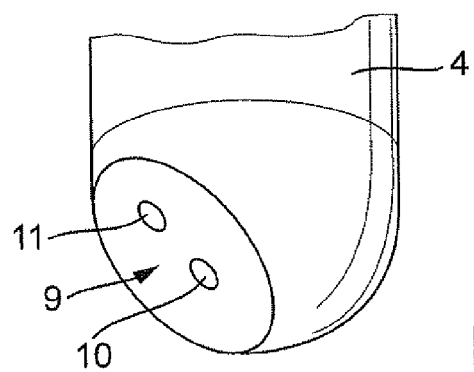
FIG. 2 an embodiment of the arrangement of the invention.

In FIG. 1a, FIG. 1b and FIG. 2, the first interface 10 and the second interface 11 are arranged at an angle, especially at 45°, to the longitudinal axis L4 of the housing 4. This inclined arrangement favors the self-cleaning of the window region 9 and possibly occurring air bubbles slide automatically away.

FIG. 2 shows a larger representation of the media-side end of the arrangement 1. It is apparent that all surfaces and edges of the housing 4 in contact with the medium 5 are smooth and rounded. This minimizes the flow resistance of the housing 4.

Figure 3A:
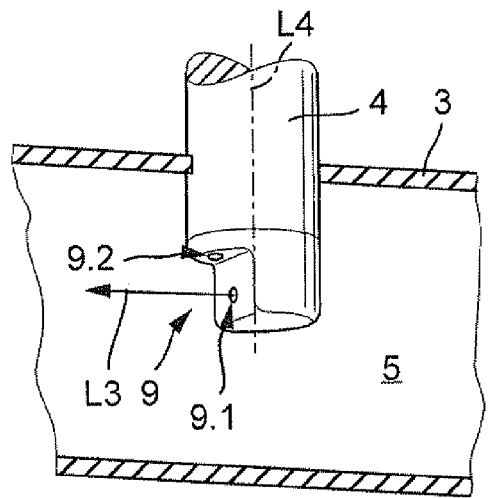
FIG. 3a another embodiment of the arrangement of the invention.
Figure 3B:
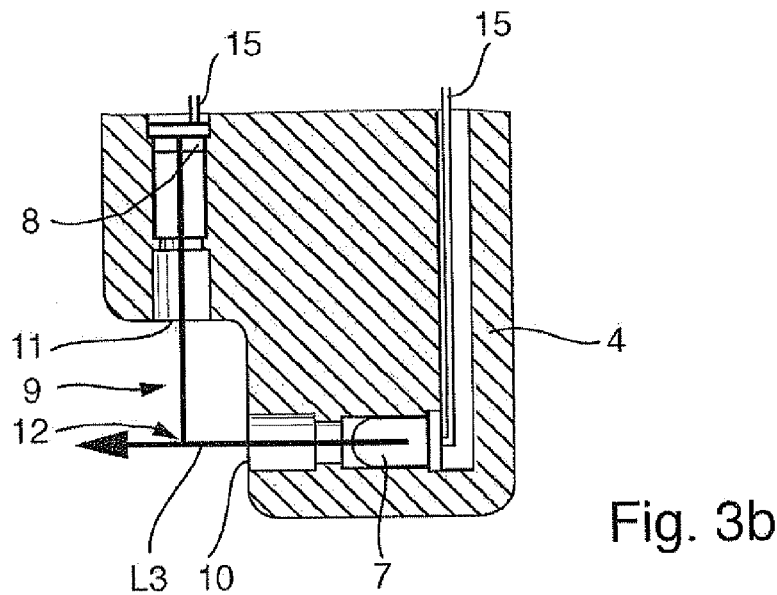
FIG. 3b the arrangement of FIG. 3a in cross section.

FIG. 3a shows another embodiment. In such case, the window region 9 is embodied with a step shape, wherein the interfaces 10 and 11 are arranged at an angle of 90° to one another. The window region 9 includes, thus, two portions 9.1, 9.2, wherein the portions are perpendicular to one another. FIG. 3b shows a cross section of this embodiment. The light source 7 is, thus, arranged perpendicularly to the longitudinal axis L4 of the housing 4 and transmits in the direction of the longitudinal axis L3 of the pipe 3. The light source 7 transmits thus from the portion 9.1 of the window region 9. The light receiver 8 is arranged parallelly to the longitudinal axis L4. The light receiver 8 thus receives through the portion 9.2 of the window region 9.

Figure 3C:
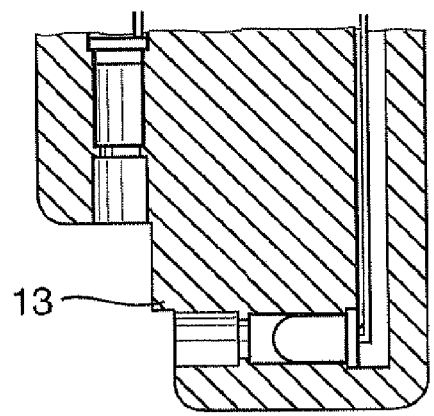
FIG. 3c arrangement of FIG. 3a in an embodiment in cross section.

In order that no direct optical crosstalk from light source 7 to light receiver 8 takes place, the housing 4 includes a protrusion 13; see FIG. 3c in this connection. There is, thus, no direct light path. In order that transmitted light reaches the receiver, it must be scattered by the medium. Light source 7 and light receiver 8 are so embodied in FIG. 3c that light scattered at 90° strikes the light receiver 8.

Figure 4A:
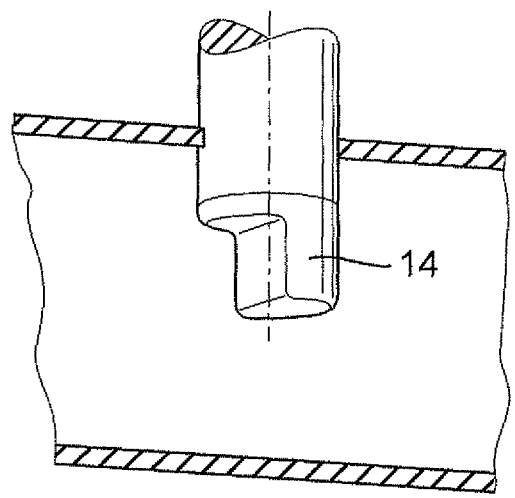
FIG. 4a another embodiment of the arrangement of the invention.
Figure 4B:
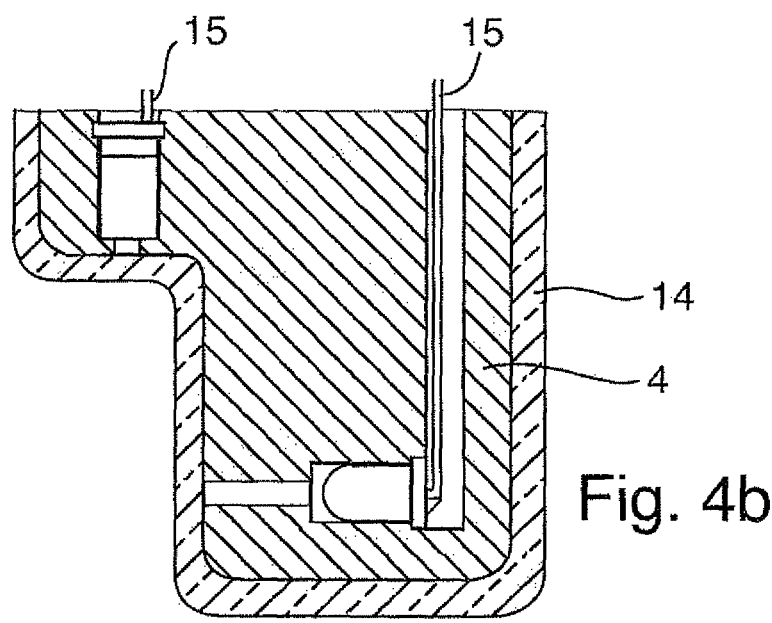
FIG. 4b the arrangement of FIG. 4a in cross section.

FIG. 4a shows another embodiment. FIG. 4b shows this in cross section. The window region 9 includes a protective shell 14. This protective shell 14 is transparent for the light and is, thus, produced, for instance, from quartz glass. If a protective shell 14 is arranged over the whole window region 9, individual windows, such as described above (compare, for instance, FIG. 2) do not need to be used. As also in the embodiment without protective shell 14, a protrusion 13 can be used to prevent direct optical crosstalk from light source 7 to light receiver 8. The outer surface, thus the medium-contacting part, forms a homogeneous body and can, thus, be cleaned relatively simply. The protective shell 14 is connected with the housing, for instance, by adhesive, soldering or by a mechanical connection with supplemental sealing.

FIG. 4a and FIG. 4b show the protective shell 14 with a step shaped window region 9. Equally, the protective shell can be used with the embodiment, in which the window region 9, especially the first and second interfaces 10, 11, are arranged at an angle to the longitudinal axis L4 (compare FIG. 2).

The invention claimed is:

1. An arrangement for optically measuring one or more physical, chemical and/or biological process variables of a medium flowing through a pipe, comprising:
   a housing having a window region, said housing structured to extend at least partially into the pipe such that the window region is disposed within the pipe, the pipe having a longitudinal direction;
   at least one light source, the light source configured to send emitted light through the window region of the housing into the medium, wherein the emitted light is directed in the medium in the longitudinal direction of the pipe and is scattered by the medium to generate scattered light having a light intensity; and
   at least one light receiver, the light receiver structured to receive the scattered light through said window region from the medium and to measure the light intensity, the light intensity being a measure for the physical, chemical and/or biological process variables,
   wherein the window region is oriented relative to the longitudinal direction such that only scattered light scattered at a desired angle with respect to the emitted light reaches the light receiver, and wherein the desired angle is 90° or 135°.

2. The arrangement as claimed in claim 1, wherein said housing is arranged essentially perpendicular to the longitudinal direction of the pipe.

3. The arrangement as claimed in claim 1, further comprising:
   a first interface with a medium-contacting outer surface provided at said window region, wherein said light source is so arranged that the emitted light propagates in the longitudinal direction of the pipe after refraction at said first interface.

4. The arrangement as claimed in claim 3, further comprising:
   a second interface with a medium-contacting outer surface provided at said window region, wherein said light receiver is so arranged that light scattered in the medium at 90° to the longitudinal direction propagates after refraction on said second interface in the direction of said light receiver.

5. The arrangement as claimed in claim 4, wherein said first interface and said second interface are arranged at an angle to the longitudinal axis of said housing.

6. The arrangement as claimed in claim 1, wherein all surfaces and edges of said housing in contact with the medium are substantially smooth with corners rounded.

7. The arrangement as claimed in claim 1, wherein said window region is step-shaped and said first interface and said second interface are arranged at an angle of 90° to one another.

8. The arrangement as claimed in claim 7, wherein said light source is arranged perpendicularly to a longitudinal axis of said housing.

9. The arrangement as claimed in claim 1, wherein said housing includes a protrusion, which is so embodied that emitted light sent from said light source does not reach said light receiver on a direct path.

10. The arrangement as claimed in claim 1, wherein:
    said window region includes a protective shell that is transparent to the emitted light and the scattered light.

11. The arrangement as claimed in claim 1, wherein the arrangement is employed in a turbidity sensor.

12. A turbidity sensor, comprising:
- an arrangement for optically measuring one or more physical, chemical and/or biological process variables of a medium flowing through a pipe, comprising:
- a housing having a window region, said housing structured to extend at least partially into the pipe such that the window region is disposed within the pipe, the pipe having a longitudinal direction;
- at least one light source, the light source configured to send emitted light through the window region of the housing into the medium, wherein the emitted light is scattered by the medium to generate scattered light having a light intensity; and
- at least one light receiver, the light receiver structured to receive the scattered light through said window region from the medium and to measure the light intensity, the light intensity being a measure for the physical, chemical and/or biological process variables, wherein the window region is oriented relative to the longitudinal direction such that only scattered light scattered at a desired angle with respect to the emitted light reaches the light receiver, wherein the emitted light is directed in the medium in the longitudinal direction of the pipe, wherein the desired angle is 90° or 135°.

13. The turbidity sensor as claimed in claim 12, for application in a low turbidity domain.

14. The turbidity sensor as claimed in claim 13, wherein the application is for measuring drinking water.

15. The turbidity sensor as claimed in claim 12, further comprising:
- a first interface with a medium-contacting outer surface provided at said window region, wherein said light source is so arranged that the emitted light propagates in the longitudinal direction of the pipe only after refraction at said first interface.

16. The turbidity sensor as claimed in claim 15, further comprising:
- a second interface with a medium-contacting outer surface provided at said window region, wherein said light receiver is so arranged that light scattered in the medium at 90° to the longitudinal direction propagates after refraction on said second interface in the direction of said light receiver.

17. The turbidity sensor as claimed in claim 16, wherein said first interface and said second interface are arranged at an angle to a longitudinal axis of said housing.

18. The turbidity sensor as claimed in claim 12, wherein all surfaces and edges of said housing in contact with the medium are substantially smooth with corners rounded.

* * * * *